(12) United States Patent
Amemiya et al.

(10) Patent No.: US 6,669,642 B2
(45) Date of Patent: Dec. 30, 2003

(54) DOPPLER SIGNAL PROCESSING APPARATUS AND ULTRASONIC DIAGNOSTIC APPARATUS

(75) Inventors: Shinichi Amemiya, Tokyo (JP); Yoichi Suzuki, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/244,578

(22) Filed: Sep. 16, 2002

(65) Prior Publication Data

US 2003/0055333 A1 Mar. 20, 2003

(30) Foreign Application Priority Data

Sep. 17, 2001 (JP) ........................................ 2001-281374

(51) Int. Cl.[7] ................................................. A61B 8/06
(52) U.S. Cl. ...................................................... 600/453
(58) Field of Search ................................ 600/437–471; 73/620–633; 367/7, 11, 130, 138; 128/916

(56) References Cited

U.S. PATENT DOCUMENTS

| 5,483,964 A | 1/1996 | Amemiya et al. |
| 5,584,294 A | 12/1996 | Amemiya et al. |
| 5,615,679 A | 4/1997 | Ri et al. |
| 5,684,484 A | 11/1997 | Suzuki |
| 5,720,708 A | * 2/1998 | Lu et al. ...................... 600/447 |
| 5,840,034 A | 11/1998 | Amemiya et al. |
| 5,879,302 A | 3/1999 | Hashimoto et al. |
| 6,139,497 A | 10/2000 | Amemiya et al. |
| 6,322,510 B1 | 11/2001 | Kataoka et al. |

FOREIGN PATENT DOCUMENTS

JP        402200257 A   *  8/1990   ............ A61B/8/06

* cited by examiner

Primary Examiner—Ali M. Imam
(74) Attorney, Agent, or Firm—Carl B. Horton, Esq.; Armstrong Teasdale LLP

(57) ABSTRACT

For the purpose of removing an effect of window processing in window-processing time-domain Doppler signals, translating them to a frequency domain, and then translating them back to the time domain, when cutting signals of a predetermined length from a time-domain Doppler signal; performing window processing on the cut signals; transforming the window-processed signals into frequency-domain signals by Fourier transformation; inversely transforming the frequency-domain signals by inverse Fourier transformation into a time-domain signal after performing predefined processing on the signals; and outputting the time-domain signal as an acoustic signal, the window processing is performed using a window having a profile with a flat top; and the cutting from the Doppler signal is performed such that a former cut signal and a latter cut signal overlap in a portion corresponding to the flat portion of the window.

20 Claims, 14 Drawing Sheets

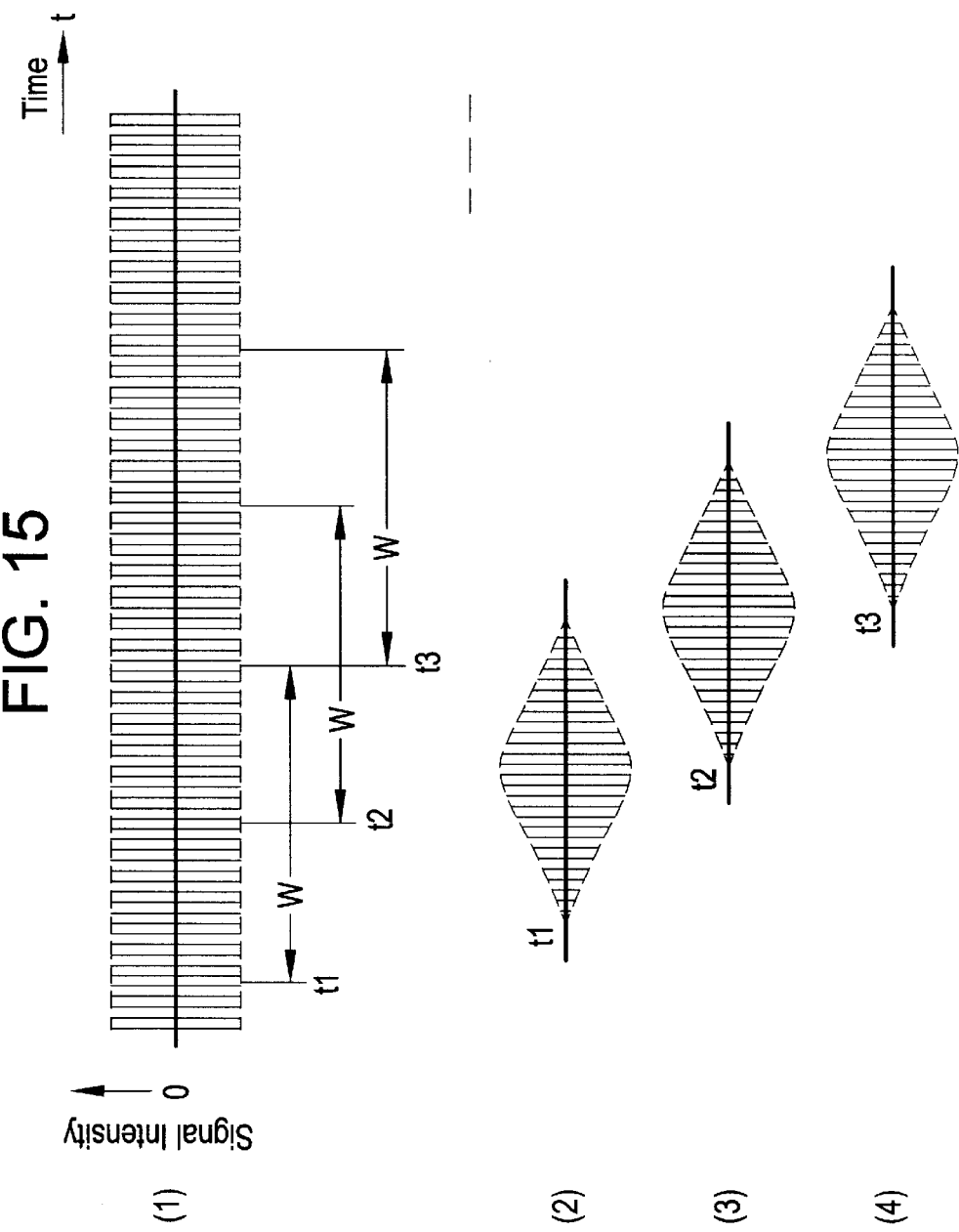

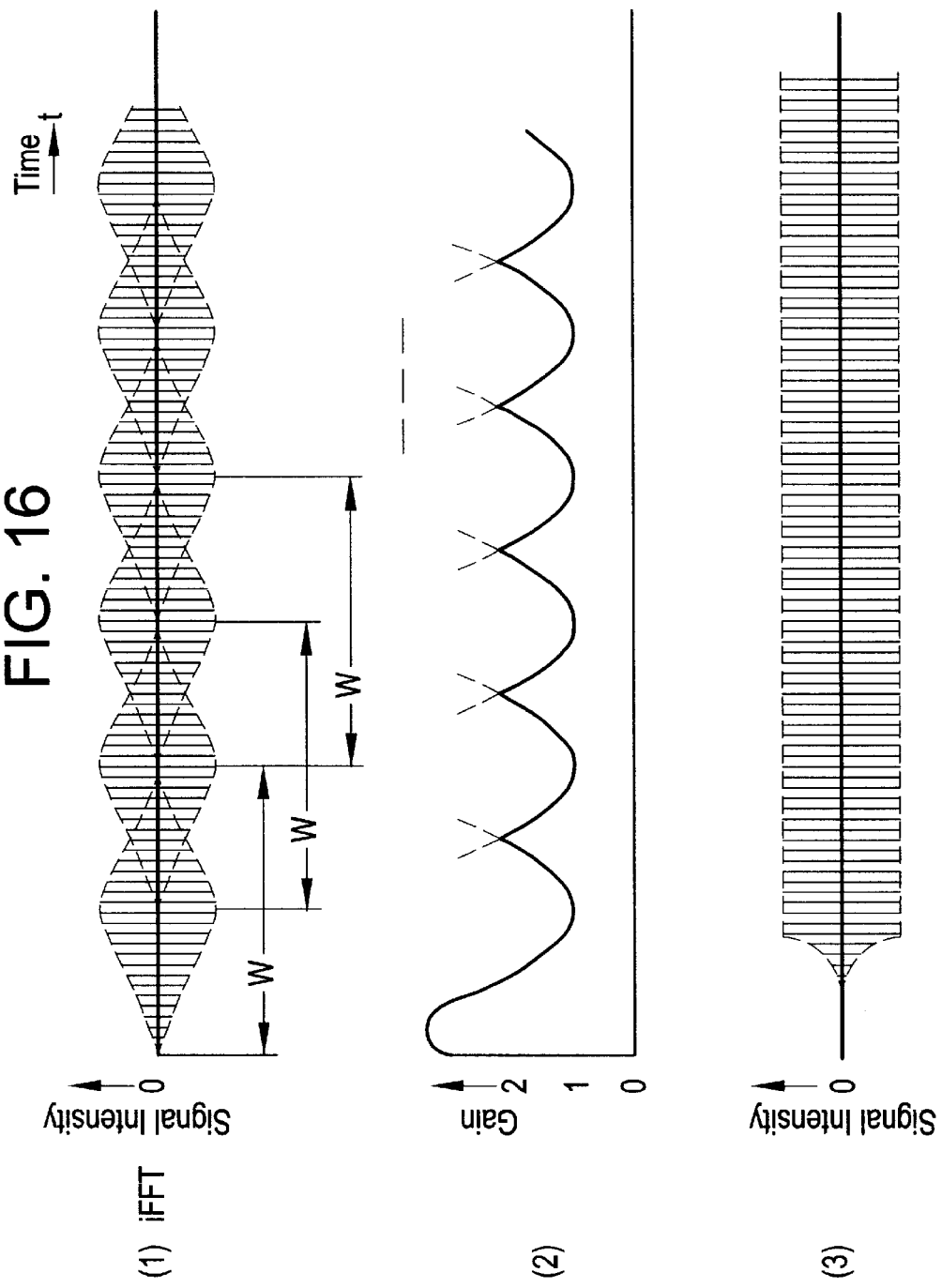

DOPPLER SIGNAL PROCESSING APPARATUS AND ULTRASONIC DIAGNOSTIC APPARATUS

CROSS REFERENCE TO RELATED APPLICATIONS

This application claims the benefit of Japanese Application No. 2001-281374 filed Sep. 17, 2001.

BACKGROUND OF THE INVENTION

The present invention relates to a Doppler signal processing method and apparatus and an ultrasonic diagnostic apparatus, and more particularly to a Doppler signal processing method and apparatus and an ultrasonic diagnostic apparatus for cutting time-domain Doppler signals of a predetermined length, window-processing the cut signals, transforming the window-processed signals into frequency-domain signals by Fourier transformation, inversely transforming the frequency-domain signals into a time-domain signal by inverse Fourier transformation after performing appropriate processing such as filtering on the signals in the frequency domain, and outputting the time-domain signal as an acoustic signal.

An ultrasonic imaging apparatus scans the interior of a subject with an ultrasonic beam; receives echoes; acquires image data corresponding to the intensity of the echoes; and thereby produces a so-called B-mode image. This process is sometimes referred to as B-mode imaging.

Moreover, the ultrasonic imaging apparatus acquires a Doppler signal of the echoes, and produces color images representing the dynamics of blood flow etc., i.e., so-called color Doppler images, based on the Doppler signals. The color Doppler images produced include a color flow mapping image that represents a two-dimensional distribution of the velocity of blood flow etc., and a power Doppler image that represents a two-dimensional distribution of the power of the Doppler signal. This process is sometimes referred to as color Doppler imaging.

The ultrasonic diagnostic apparatus also performs Fourier transformation on the Doppler signal of echoes from a sample volume defined in the interior of the subject to obtain a frequency spectrum. This process is sometimes referred to as point Doppler measurement.

The results of the B-mode imaging, color Doppler imaging and point Doppler measurement are displayed as respective images for use as visual information to diagnose the subject. The point Doppler measurement also outputs the Doppler signal as an acoustic signal via an audio device such as a speaker, for use as acoustic information for the diagnosis.

The signal input to the audio device is a time-domain Doppler signal before the Fourier transformation or a signal obtained by inversely Fourier-transforming the frequency spectrum back into a time-domain signal.

An FFT (fast Fourier transformer) is used for the Fourier transformation from the time domain into the frequency domain. An iFFT (inverse fast Fourier transformer) is used for the inverse Fourier transformation from the frequency domain back into the time domain.

In performing the Fourier transformation by the FFT, a temporally continuous Doppler signal is cut into signals of a predetermined length, and the cut signals are subject to window-processing for mitigating discontinuity between the signals at the cut boundaries. The window employed is, for example, a Hanning window. The window-processed Doppler signal is amplitude-modulated according to the profile of the window.

Accordingly, the signal obtained from the inverse Fourier transformation becomes a Doppler signal amplitude-modulated according to the window profile, and the acoustic signal based on such a Doppler signal is inaccurate.

SUMMARY OF THE INVENTION

Therefore, an object of the present invention is to provide a Doppler signal processing method and apparatus and an ultrasonic diagnostic apparatus for window-processing the time-domain Doppler signals, translating the signals to a frequency domain, and then translating them back to the time domain, the Doppler signal processing method and apparatus and the ultrasonic diagnostic apparatus being capable of removing an effect of the window processing.

(1) The present invention, in accordance with one aspect thereof for solving the problem, is a Doppler signal processing method for cutting signals of a predetermined length from a time-domain Doppler signal; performing window processing on said cut signals; transforming said window-processed signals into frequency-domain signals by Fourier transformation; inversely transforming said transformed frequency-domain signals into a time-domain signal by inverse Fourier transformation after performing predefined processing on said signals; and outputting said inversely transformed time-domain signal as an acoustic signal, characterized in that: said window processing is performed using a window having a profile with a flat top; and said cutting from the Doppler signal is performed such that a former cut signal and a latter cut signal overlap in a portion corresponding to the flat portion of said window.

(2) The present invention, in accordance with another aspect thereof for solving the problem, is a Doppler signal processing apparatus for cutting signals of a predetermined length from a time-domain Doppler signal; performing window processing on said cut signals; transforming said window-processed signals into frequency-domain signals by Fourier transformation; inversely transforming said transformed frequency-domain signals into a time-domain signal by inverse Fourier transformation after performing predefined processing on said signals; and outputting said inversely transformed time-domain signal as an acoustic signal, characterized in comprising: window processing means for performing said window processing using a window having a profile with a flat top; and signal cutting means for performing said cutting from the Doppler signal such that a former cut signal and a latter cut signal overlap in a portion corresponding to the flat portion of said window.

(3) The present invention, in accordance with still another aspect thereof for solving the problem, is an ultrasonic diagnostic apparatus for transmitting ultrasound and acquiring a Doppler signal of an echo of the ultrasound; cutting signals of a predetermined length from said Doppler signal in a time domain; performing window processing on said cut signals; transforming said window-processed signals into frequency-domain signals by Fourier transformation; inversely transforming said transformed frequency-domain signals into a time-domain signal by inverse Fourier transformation after performing predefined processing on said signals; and outputting said inversely transformed time-domain signal as an acoustic signal, characterized in comprising: window processing means for performing said window processing using a window having a profile with a flat top; and signal cutting means for performing said cutting from the Doppler signal such that a former cut signal and a latter cut signal overlap in a portion corresponding to the flat portion of said window.

In the invention of the aspects (1)–(3), since the window processing is performed using a window having a profile with a flat top and the cutting from the Doppler signal is performed such that a former cut signal and a latter cut signal overlap in a portion corresponding to the flat portion of the window, the Doppler signals translated from the frequency domain to the time domain connect at the flat portion of the window. Thus, an effect of the window processing can be removed.

Preferably, the profile of the window is generally trapezoidal so that discontinuity between the signals due to the cutting can be mitigated.

(4) The present invention, in accordance with still another aspect thereof for solving the problem, is a Doppler signal processing method for cutting signals of a predetermined length from a time-domain Doppler signal; performing window processing on said cut signals; transforming said window-processed signals into frequency-domain signals by Fourier transformation; inversely transforming said transformed frequency-domain signals into a time-domain signal by inverse Fourier transformation after performing predefined processing on said signals; and outputting said inversely transformed time-domain signal as an acoustic signal, characterized in comprising: performing amplitude modulation with a property opposite to that of amplitude modulation by said window processing before outputting said inversely-transformed time-domain signal as the acoustic signal.

(5) The present invention, in accordance with still another aspect thereof for solving the problem, is a Doppler signal processing apparatus for cutting signals of a predetermined length from a time-domain Doppler signal; performing window processing on said cut signals; transforming said window-processed signals into frequency-domain signals by Fourier transformation; inversely transforming said transformed frequency-domain signals into a time-domain signal by inverse Fourier transformation after performing predefined processing on said signals; and outputting said inversely transformed time-domain signal as an acoustic signal, characterized in comprising: amplitude modulating means for performing amplitude modulation with a property opposite to that of amplitude modulation by said window processing before outputting said inversely-transformed time-domain signal as the acoustic signal.

(6) The present invention, in accordance with still another aspect thereof for solving the problem, is an ultrasonic diagnostic apparatus for transmitting ultrasound and acquiring a Doppler signal of an echo of the ultrasound; cutting signals of a predetermined length from said Doppler signal in a time domain; performing window processing on said cut signals; transforming said window-processed signals into frequency-domain signals by Fourier transformation; inversely transforming said transformed frequency-domain signals into a time-domain signal by inverse Fourier transformation after performing predefined processing on said signals; and outputting said inversely transformed time-domain signal as an acoustic signal, characterized in comprising: amplitude modulating means for performing amplitude modulation with a property opposite to that of amplitude modulation by said window processing before outputting said inversely-transformed time-domain signal as the acoustic signal.

In the invention of the aspects (4)–(6), since amplitude modulation with a property opposite to that of amplitude modulation by the window processing is performed before outputting the time-domain signal as the acoustic signal obtained by the inverse transformation, an effect of the window processing can be removed.

The window for performing the window processing on said cut signals is preferably a Hanning window so that discontinuity of the signals at the cut boundaries can be eliminated.

The predefined processing is preferably filtering processing so that unwanted signal components can be removed.

The predefined processing is preferably zero-shifting processing so that aliasing of the Doppler signal can be corrected.

The predefined processing is preferably correction processing of the output characteristics of said acoustic signal so that fidelity of the acoustic signal can be improved.

Therefore, the present invention can provide a Doppler signal processing method and apparatus and an ultrasonic diagnostic apparatus for window-processing time-domain Doppler signals, translating the signals to a frequency domain, and then translating them back to the time domain, the Doppler signal processing method and apparatus and the ultrasonic diagnostic apparatus being capable of removing an effect of the window processing.

Further objects and advantages of the present invention will be apparent from the following description of the preferred embodiments of the invention as illustrated in the accompanying drawings.

BRIEF DESCRIPTION OF THE DRAWINGS

FIG. 15 shows the relationship between Doppler signal cutting and window processing.

FIG. 16 shows restoration of Doppler signal.

DETAILED DESCRIPTION OF THE INVENTION

Figure 1:
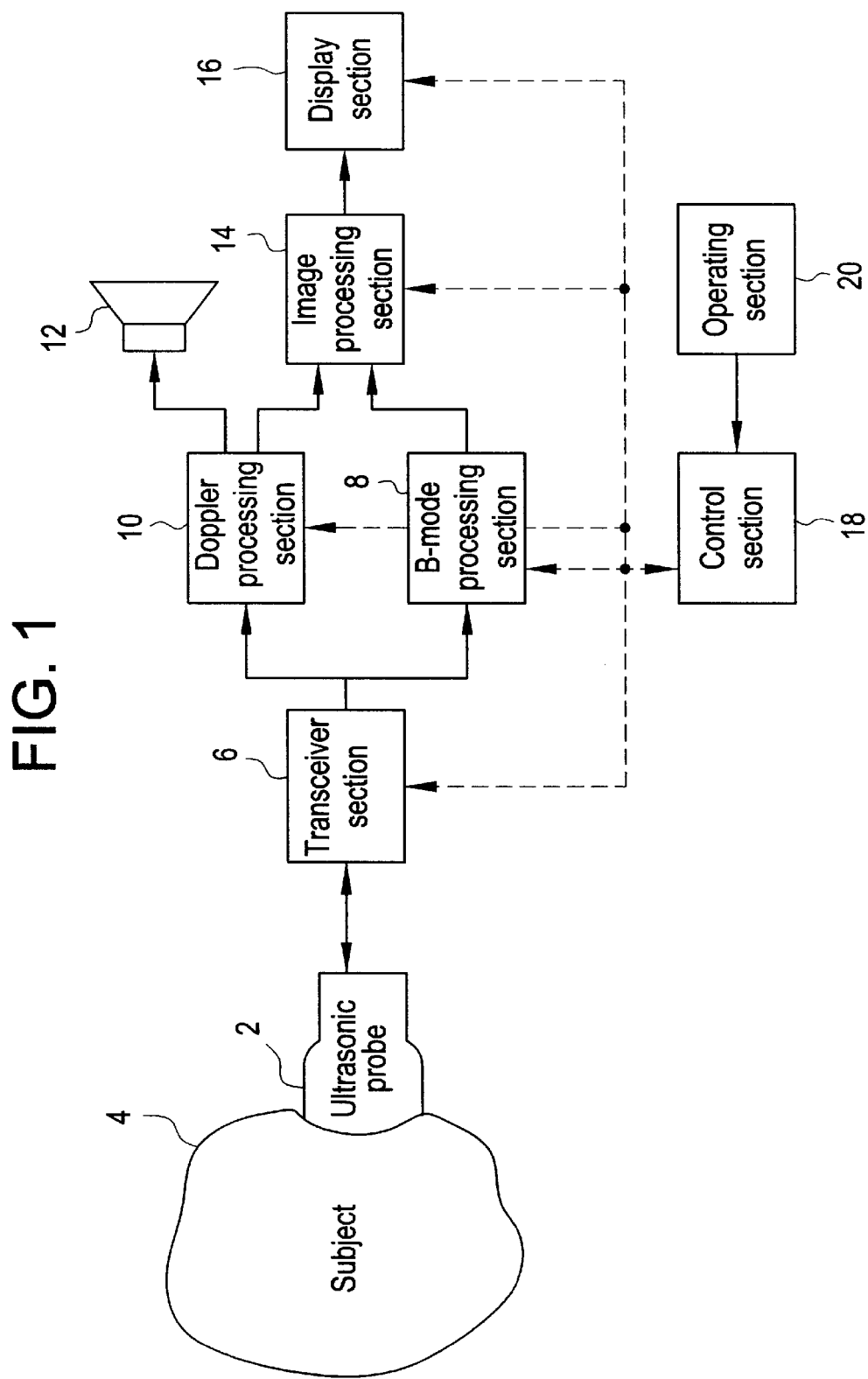
FIG. 1 is a block diagram of an apparatus in accordance with one embodiment of the present invention.

Several embodiments of the present invention will now be described in detail with reference to the accompanying drawings. FIG. 1 shows a block diagram of an ultrasonic imaging apparatus, which is an embodiment of the present invention. The configuration of the apparatus represents an embodiment of the apparatus in accordance with the present invention. The operation of the apparatus represents an embodiment of the method in accordance with the present invention.

As shown in FIG. 1, the present apparatus has an ultrasonic probe 2. The ultrasonic probe 2 has an array of ultrasonic transducers (not shown). The individual ultrasonic transducers are made from a piezoelectric material such as PZT (lead zirconate titanate [Pb—Zr—Ti]) ceramic. The ultrasonic probe 2 is used abutted against a subject 4 by a user.

The ultrasonic probe 2 is connected to a transceiver section 6. The transceiver section 6 supplies driving signals to the ultrasonic probe 2 to transmit ultrasound. It also receives echo signals picked up by the ultrasonic probe 2.

Figure 2:
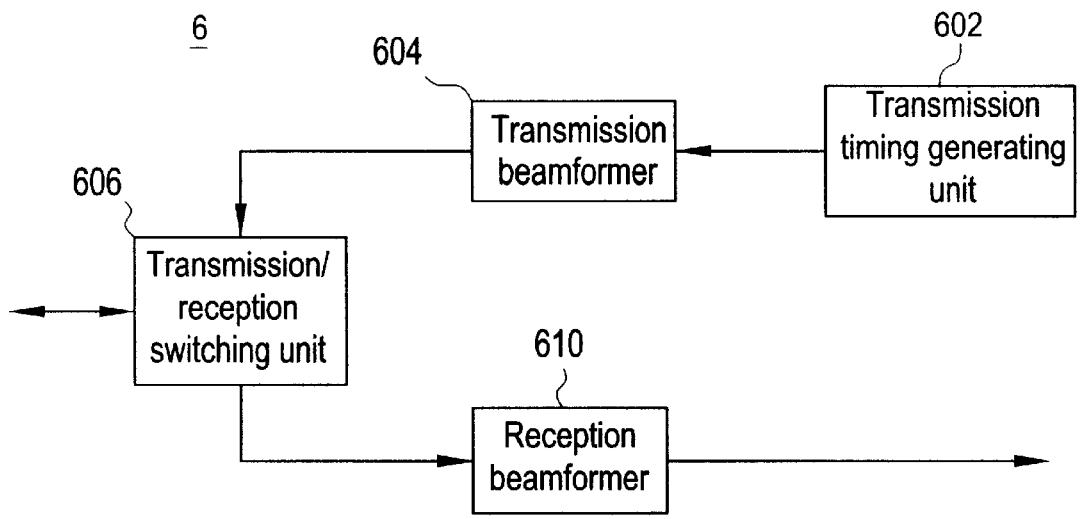
FIG. 2 is a block diagram of a transceiver section.

FIG. 2 shows a block diagram of the transceiver section 6. As shown, the transceiver section 6 has a transmission timing generating unit 602. The transmission timing generating unit 602 periodically generates a transmission timing signal, and inputs the signal to a transmission beamformer 604.

The transmission beamformer 604 is for performing beamforming for the transmission, and generates a beamforming signal for forming an ultrasonic beam in a certain direction based on the transmission timing signal. The beamforming signal includes a plurality of driving signals that are given respective time differences corresponding to the direction. The beamforming is controlled by a control section 18, which will be described later. The transmission beamformer 604 inputs the transmission beamforming signal to a transmission/reception switching unit 606.

The transmission/reception switching unit 606 inputs the beamforming signal to the ultrasonic transducer array. A plurality of ultrasonic transducers that constitute a transmission aperture in the ultrasonic transducer array generate ultrasound having respective phase differences corresponding to the time differences in the driving signals. By wavefront synthesis of the ultrasound, an ultrasonic beam is formed along an acoustic line in a certain direction.

The transmission/reception switching unit 606 is connected with a reception beamformer 610. The transmission/reception switching unit 606 inputs the echo signals picked up by a reception aperture in the ultrasonic transducer array to the reception beamformer 610.

The reception beamformer 610 is for performing beamforming for the reception corresponding to an acoustic line for the transmission, involving imparting time differences to a plurality of received echoes to adjust their phases, and then adding the echoes to form an echo received signal along an acoustic line in a certain direction. The reception beamforming is controlled by the control section 18, which will be described later.

The transmission of the ultrasonic beam is repeated at predefined time intervals in response to the transmission timing signal generated by the transmission timing generating unit 602. Synchronously with the timing, the transmission beamformer 604 and the reception beamformer 610 change the direction of the acoustic line by a predefined amount. Thus, the interior of the subject 4 is sequentially scanned by the acoustic line.

Figure 3:
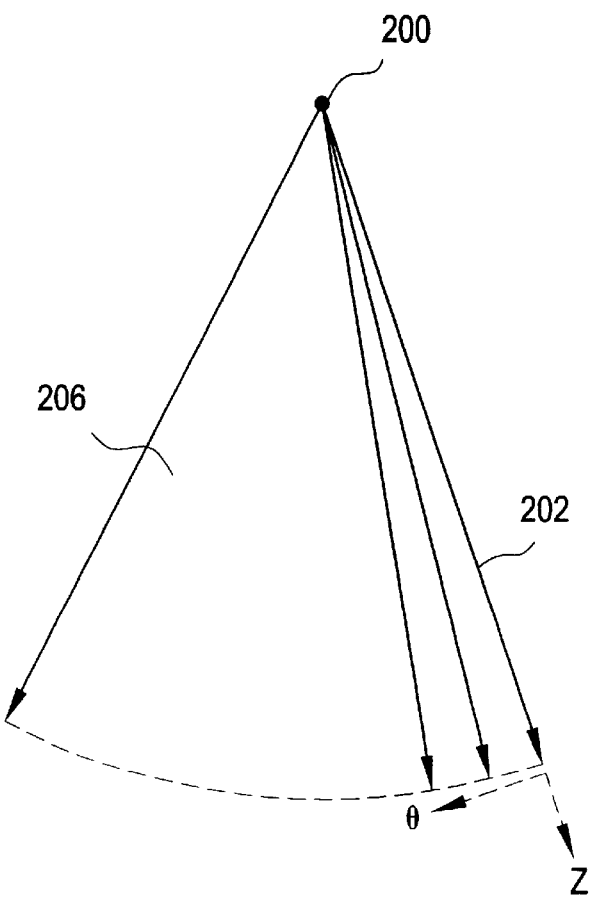
FIG. 3 is a diagram showing the concept of scanning by the transceiver section.

The transceiver section 6 having such a configuration performs a scan as exemplarily shown in FIG. 3. Specifically, a fan-shaped two-dimensional region 206 is scanned in the O-direction by an acoustic line 202 extending from an emission point 200 in the z-direction, and a so-called sector scan is carried out.

Figure 4:
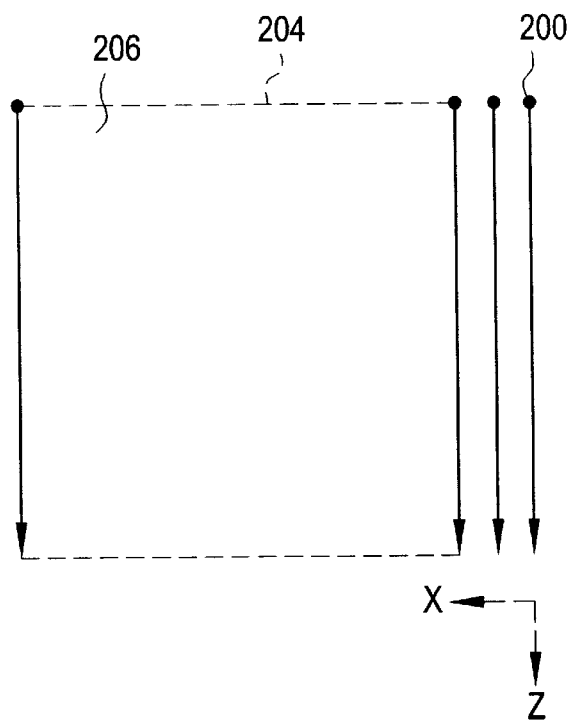
FIG. 4 is a diagram showing the concept of scanning by the transceiver section.

When the transmission and reception apertures are formed using part of the ultrasonic transducer array, a scan as exemplarily shown in FIG. 4 can be performed by sequentially shifting the apertures along the array. Specifically, a rectangular two-dimensional region 206 is scanned in the x-direction by translating an acoustic line 202, which travels from an emission point 200 in the z-direction, along a linear trajectory 204, and a so-called linear scan is carried out.

Figure 5:
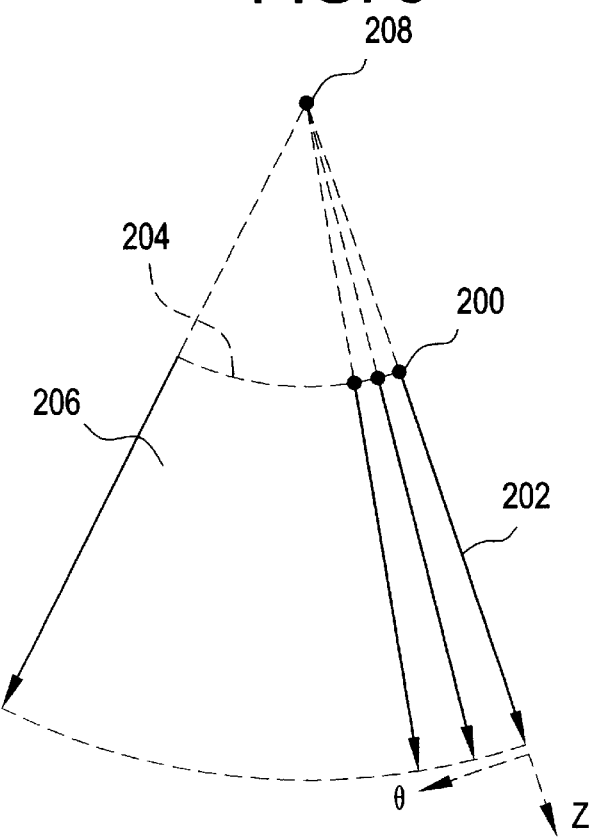
FIG. 5 is a diagram showing the concept of scanning by the transceiver section.

It will be easily recognized that when the ultrasonic transducer array is a so-called convex array, which is formed along an arc protruding in the direction of ultrasound transmission, a partial fan-shaped two-dimensional region 206 can be scanned in the O-direction by performing an acoustic line scan similar to that for the linear scan and moving an emission point 200 of an acoustic line 202 along an arc-like trajectory 204, as exemplarily shown in FIG. 5, and a so-called convex scan is carried out.

The transceiver section 6 is connected to a B-mode processing section 8 and a Doppler processing section 10. The echo received signal for each acoustic line output from the transceiver section 6 is input to the B-mode processing section 8 and the Doppler processing section 10.

Figure 6:
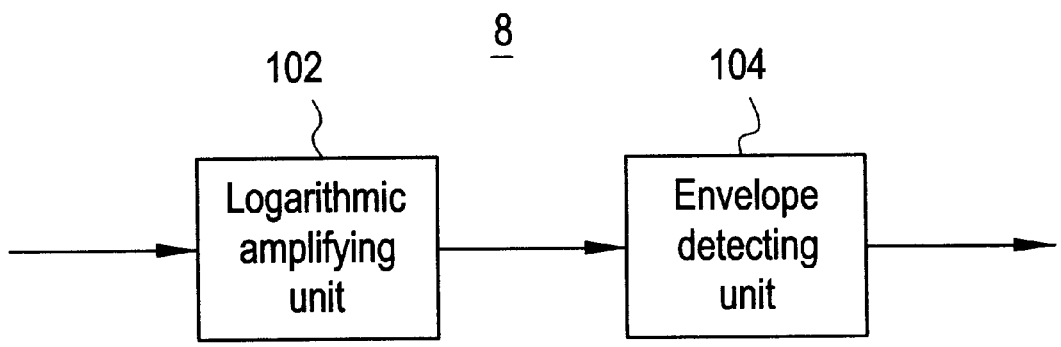
FIG. 6 is a block diagram of a B-mode processing section.

The B-mode processing section 8 is for generating B-mode image data. The B-mode processing section 8 comprises a logarithmic amplifying unit 102 and an envelope detecting unit 104, as shown in FIG. 6.

The B-mode processing section 8 logarithmically amplifies the echo received signal at the logarithmic amplifying unit 102, and detects its envelope at the envelope detecting unit 104 to acquire a signal indicating the intensity of the echo at each reflection point on an acoustic line, i.e., an A-scope signal; and generates B-mode image data using the amplitude of the A-scope signal at each instant as the brightness.

The Doppler processing section 10 is for generating Doppler image data, Doppler frequency data and a Doppler signal for sound output. The Doppler image data includes flow velocity data, variance data and power data, which will be described later.

Figure 7:
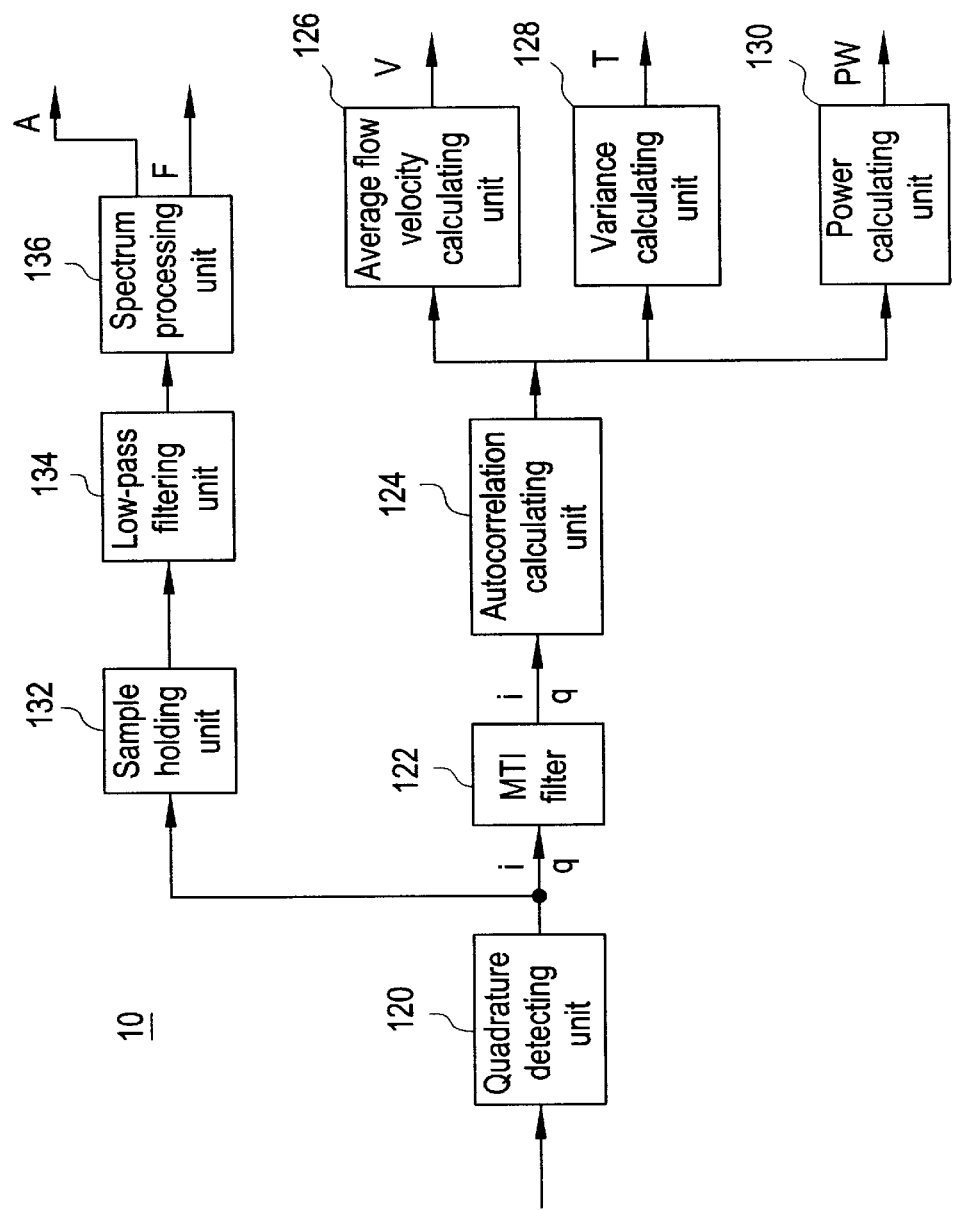
FIG. 7 is a block diagram of a Doppler processing section.

As shown in FIG. 7, the Doppler processing section 10 comprises a quadrature detecting unit 120, an MTI (moving target indication) filter 122, an autocorrelation calculating unit 124, an average flow velocity calculating unit 126, a variance calculating unit 128 and a power calculating unit 130. Moreover, it further comprises a sample holding unit 132, a low-pass filtering unit 134, and a spectrum processing unit 136.

The Doppler processing section 10 quadrature-detects the echo received signal at the quadrature detecting unit 120. A carrier signal employed for the quadrature detection is a signal having a frequency equal to the fundamental frequency of the transmitted ultrasound.

The Doppler processing section 10 MTI-processes the quadrature-detected echo at the MTI filter 122 to obtain a Doppler signal. The MTI processing is performed using a plurality of echoes acquired by a plurality of times of the ultrasound transmission/reception per acoustic line. The number of times of the transmission/reception per acoustic line is, for example, eight.

The Doppler processing section 10 also performs an autocorrelation calculation on the output signal from the MTI filter 122 at the autocorrelation calculating unit 124; calculates an average flow velocity V from the result of the autocorrelation calculation at the average flow velocity calculating unit 126; calculates a variance T of the flow velocity from the result of the autocorrelation calculation at the variance calculating unit 128; and calculates a power PW of the Doppler signal from the result of the autocorrelation calculation at the power calculating unit 130. The average flow velocity will sometimes be referred to simply as the flow velocity hereinbelow. Moreover, the variance of the flow velocity will sometimes be referred to simply as the variance, and the power of the Doppler signal simply as the power hereinbelow.

Such data processing gives data representing the flow velocity V, variance T and power PW of an echo source moving inside the subject 4 for each acoustic line. The data represents the flow velocity, variance and power at each point (pixel) on an acoustic line. The flow velocity is obtained as a component in an acoustic line direction, and a direction approaching the ultrasonic probe 2 and a direction going away from the ultrasonic probe 2 are distinguished.

The sample holding unit 132 sample-holds a portion of an echo that is generated from a sample volume predefined within the subject 4. Such sample holding is sometimes referred to as range gate sampling.

The sample holding is performed for each of the plurality of echoes acquired by the plurality of times of the ultrasound transmission/reception for an acoustic line. The number of times of the transmission/reception is, for example, 128. This gives 128 sampling data points, for example. A sequence of the data points represents a Doppler signal.

The Doppler signal is low-pass filtered at the low-pass filtering unit 134, and then spectrum-processed at the spectrum processing unit 136 to provide a frequency spectrum F and a Doppler signal for sound output A. The spectrum processing unit 136 will be later described in detail.

The B-mode processing section 8 and the Doppler processing section 10 are connected to an image processing section 14. The image processing section 14 produces a B-mode image, Doppler image and frequency spectrum image based on respective data supplied from the B-mode processing section 8 and the Doppler processing section 10.

The Doppler processing section 10 is connected with a sound outputting section 12. The Doppler processing unit 10 supplies the Doppler signal to the sound outputting section 12. Thus, the Doppler signal is output as an audible sound via the sound outputting section 12. The sound outputting section 12 employed is a speaker, for example.

Figure 8:
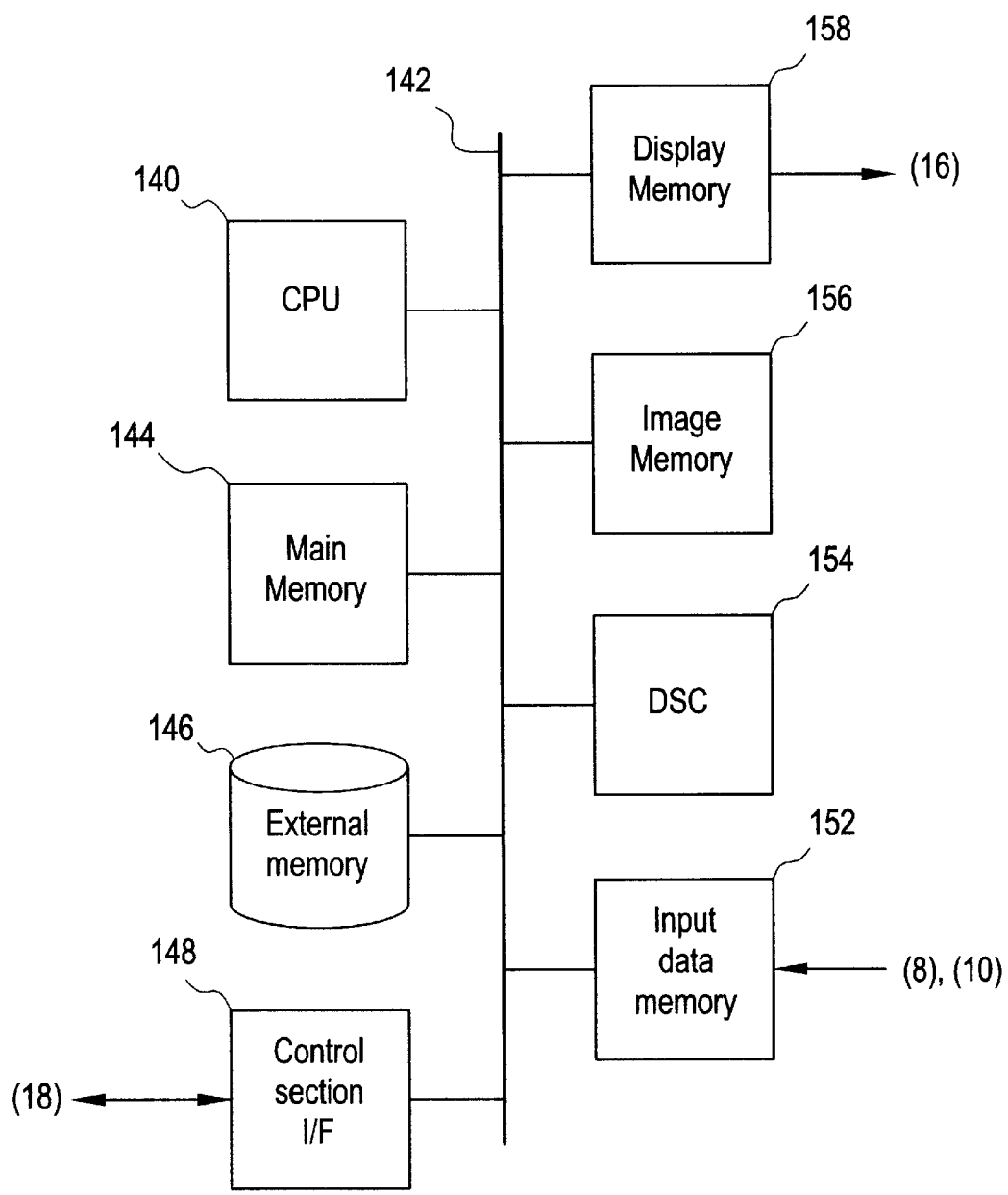
FIG. 8 is a block diagram of an image processing section.

The image processing section 14 comprises a central processing unit (CPU) 140, as shown in FIG. 8. The CPU 140 is connected with a main memory 144, an external memory 146, a control section interface 148, an input data memory 152, a digital scan converter (DSC) 154, an image memory 156 and a display memory 158 via a bus 142.

The external memory 146 stores programs executed by the CPU 140. It also stores several kinds of data for use by the CPU 140 in executing the programs.

The CPU 140 carries out predefined image processing by loading a program from the external memory 146 into the main memory 144 for execution. The CPU 140 communicates control signals with the control section 18, which will be described later, via the control section interface 148 in the course of the program execution.

The B-mode image data, Doppler image data and frequency spectrum data for each acoustic line supplied from the B-mode processing section 8 and the Doppler processing section 10 are stored in the input data memory 152. The data in the input data memory 152 are scan-converted at the DSC 154 and stored in the image memory 156. The data in the image memory 156 are output to a display section 16 via the display memory 158.

The image processing section 14 is connected with the display section 16. The display section 16 is supplied with image data from the image processing section 14, and displays an image based on the image data. The display section 16 comprises a graphic display or the like employing a CRT capable of displaying a color image.

The transceiver section 6, B-mode processing section 8, Doppler processing section 10, image processing section 14 and display section 16 are connected with the control section 18. The control section 18 supplies control signals to these sections to control their operation. The control section 18 is supplied with several kinds of notification signals from the controlled sections. The B-mode operation and the Doppler-mode operation are executed under control of the control section 18.

The control section 18 is connected with an operating section 20. The operating section 20 is operated by the user, and the section 20 inputs appropriate instructions and information to the control section 18. The operating section 20 comprises, for example, a keyboard, pointing device and other operating devices.

Now the imaging operation of the present apparatus will be described. The user abuts the ultrasonic probe 2 against a desired portion on the subject 4, and operates the operating section 20 to conduct imaging operation in, for example, a B-mode and a Doppler mode combined. Thus, B-mode imaging and Doppler-mode imaging are conducted in a time-sharing manner under control of the control section 18. Specifically, a combined scan in the B-mode and the Doppler mode is performed at a rate of, for example, a scan in the B-mode conducted once every so many scans in the Doppler mode.

In the B-mode, the transceiver section 6 scans the interior of the subject 4 sequentially for every acoustic line and receives an echo each time through the ultrasonic probe 2. The B-mode processing section 8 logarithmically amplifies the echo received signal supplied from the transceiver section 6 at the logarithmic amplifying unit 102; envelope-detects the signal at the envelope detecting unit 104 to acquire an A-scope signal; and generates B-mode image data for each acoustic line based on the A-scope signal.

The image processing section 14 stores the B-mode image data for each acoustic line supplied from the B-mode processing section 8 in the input data memory 152. Thus, an acoustic line data space for the B-mode image data is formed in the input data memory 152.

In the Doppler mode, the transceiver section 6 scans the interior of the subject 4 sequentially for every acoustic line and receives an echo each time through the ultrasonic probe 2. In the scanning, the ultrasound transmission and echo reception are conducted a plurality of times per acoustic line. Moreover, a predetermined number of times of ultrasound transmission/reception are conducted for the acoustic line passing through the predefined sample volume.

The Doppler processing section 10 quadrature-detects the echo received signal at the quadrature detecting unit 120; MTI-processes the signal at the MTI filter 122; calculates an autocorrelation at the autocorrelation calculating unit 124; calculates from the result of the autocorrelation calculation a flow velocity V at the average flow velocity calculating unit 126, a variance T at the variance calculating unit 128 and a power PW at the power calculating unit 130. These calculated values constitute data representing the velocity, variance and power of an echo source for each acoustic line and for each pixel.

Moreover, the Doppler processing section 10 sample-holds the output signal from the quadrature detecting unit 120 at the sample holding unit 132, performs low-pass filtering at the low-pass filtering unit 134, and performs spectrum processing at the spectrum processing unit 136. The spectrum processing will be later described in detail.

The image processing section 14 stores the Doppler image data for each acoustic line and for each pixel supplied from the Doppler processing section 10 in the input data memory 152. It also stores the frequency spectrum data supplied from the Doppler processing section 10 in the input data memory 152. Thus, an acoustic line data space and a frequency spectrum data space for the Doppler image data are formed in the input data memory 152.

The CPU 140 scan-converts the B-mode image data, Doppler image data and frequency spectrum data in the input data memory 152 at the DSC 154, and writes the scan-converted data into the image memory 156.

In writing the data, the Doppler image data are written as flow velocity distribution image data in which the flow velocity V and the variance T are combined, power Doppler image data employing the power PW or power Doppler image data with variance in which the power PW and the variance T are combined, and variance image data employing the variance T.

The CPU 140 writes the B-mode image data, Doppler image data and frequency spectrum data into separate regions. Then, images based on the B-mode image data, Doppler image data and frequency spectrum data are displayed on the display section 16 via the display memory 158.

The B-mode image represents a cross-sectional image of an internal tissue in an acoustic line scan plane. The flow velocity distribution image of the color Doppler images represents a two-dimensional distribution of the flow velocity of the echo source. This image is sometimes referred to as a color flow mapping image. In this image, the display color is differentiated according to the flow direction; the brightness of the display color is differentiated according to the flow velocity; and the purity of the display color is changed by increasing the amount of a certain color to be mixed according to the variance.

The power Doppler image represents a two-dimensional distribution of the power of the Doppler signal. The image indicates the location of a moving echo source. The brightness of the display color for the image corresponds to the power. If the variance is combined with the power, the purity of the display color is changed by increasing the amount of a certain color to be mixed according to the variance. The variance image represents a two-dimensional distribution of the variance value. This image also indicates the location of a moving echo source. The brightness of the display color corresponds to the magnitude of the variance.

In displaying these images on the display section 16, each image is superimposed on the B-mode image at the display memory 158 to display a composite image on the display section 16. Thus, a color Doppler image that distinctly indicates a position relationship relative to the internal tissue can be observed.

The frequency spectrum image is displayed in a predefined area in the display screen. The frequency spectrum image represents the frequency spectrum of the Doppler signal. If the blood flow etc. in the sample volume pulsates, the frequency spectrum varying with the pulsation is displayed in real time. Moreover, the Doppler signal having such a spectrum is output as an audible sound from the sound outputting section 12.

Figure 9:
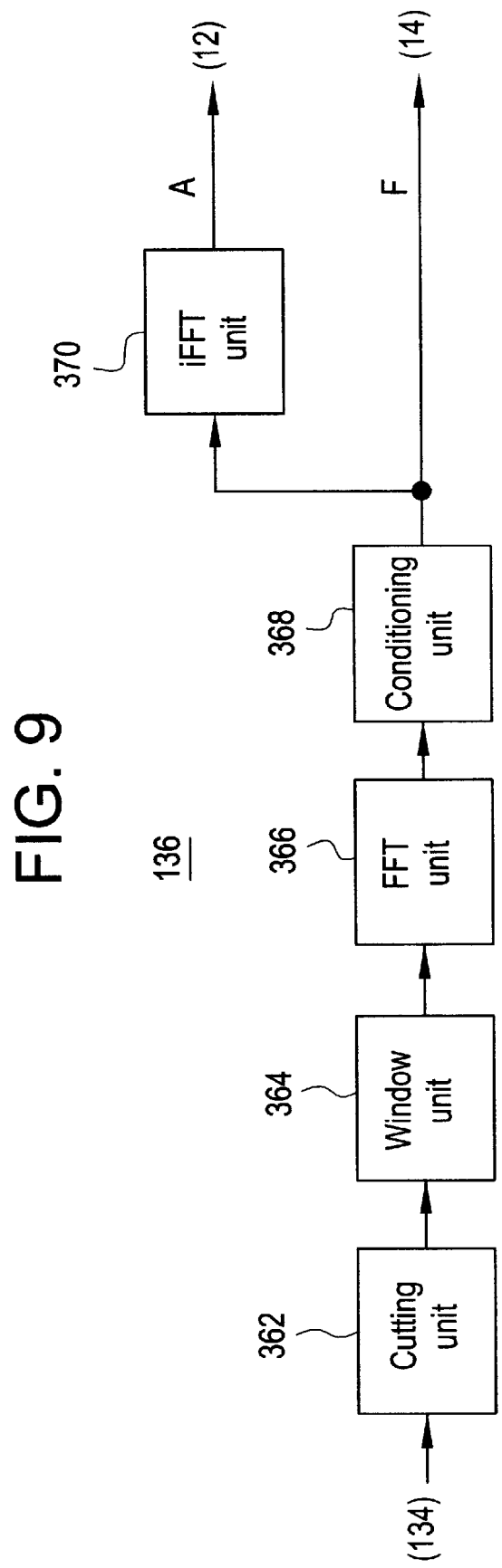
FIG. 9 is a block diagram of an exemplary spectrum processing unit.

FIG. 9 shows a detailed block diagram of an exemplary spectrum processing unit 136, which is an embodiment of the Doppler signal processing apparatus in accordance with the present invention. The configuration of the apparatus represents an embodiment of the apparatus in accordance with the present invention. The operation of the apparatus represents an embodiment of the method in accordance with the present invention.

As shown, the spectrum processing unit 136 comprises a cutting unit 362, a window unit 364, an FFT unit 366, a conditioning unit 368 and an iFFT unit 370.

The cutting unit 362 cuts signals of a predetermined length from the Doppler signal supplied from the low-pass filtering unit 134. The length of a cut signal is, for example, 32 in terms of number of the data sampling points.

The window unit 364 performs window processing on the signals supplied by the cutting unit 362 and then inputs them to the FFT unit 366. The FFT unit 366 transforms the input signals from the time domain signals into the frequency domain signals by Fourier transformation. This gives the frequency spectrum of the Doppler signal. The frequency spectrum is input to the image processing section 14 via the conditioning unit 368.

The conditioning unit 368 performs conditioning on the frequency spectrum. An example of the conditioning is filtering. The filtering to be performed is high-pass filtering. This removes a frequency spectrum originating from the motion of the internal tissue, thereby achieving a so-called wall filter function.

Another example of the conditioning is zero shifting, which is processing for shifting the zero point of a frequency spectrum. The zero shifting is performed to correct wraparound of the frequency spectrum due to aliasing.

Still another example of the conditioning is processing for correcting the output characteristics of the sound outputting section 12. When the output characteristics of the sound outputting section 12, which is, for example, a speaker, is known in advance, correction to cancel the output characteristics can be made on the frequency spectrum to improve fidelity of the acoustic signal.

The frequency spectrum output from the conditioning unit 368 is input to the image processing section 14. The frequency spectrum is also input to the iFFT unit 370, where the frequency domain signals are transformed into a time-domain signal by inverse Fourier transformation, and the transformed signal is input to the sound outputting section 12.

In the spectrum processing unit 136 having such a configuration, the window unit 364 performs the window processing using a window having a profile with a flat top.

Figure 10:
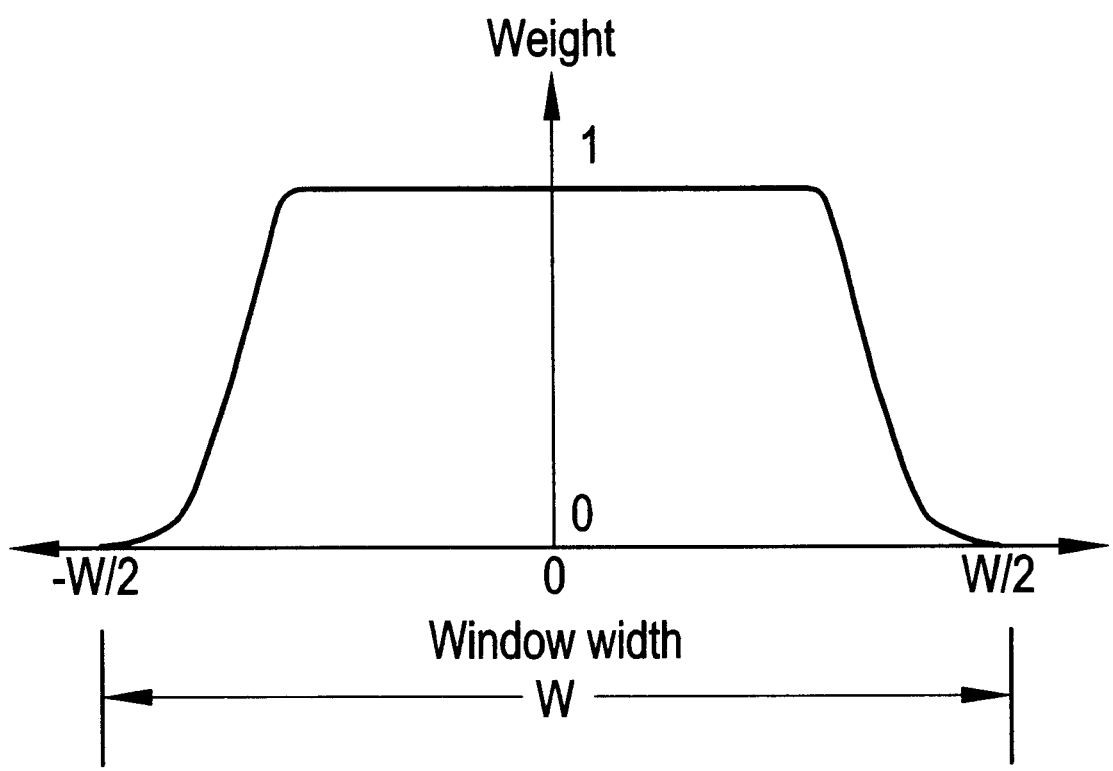
FIG. 10 shows an exemplary window profile.

FIG. 10 shows an exemplary window profile. As shown, the window profile has a weighting factor of one over a predefined length in the right and left directions from the center of the window, and the weighting factor continuously decreases to zero beyond the predefined length. In other words, the profile is generally trapezoid-shaped. The length of the top side of the trapezoid accounts for, for example, more than 50% of the window width W. It should be noted that the shape of the profile is not limited to a trapezoid, but may be any other shape with a flat top.

Figure 11:
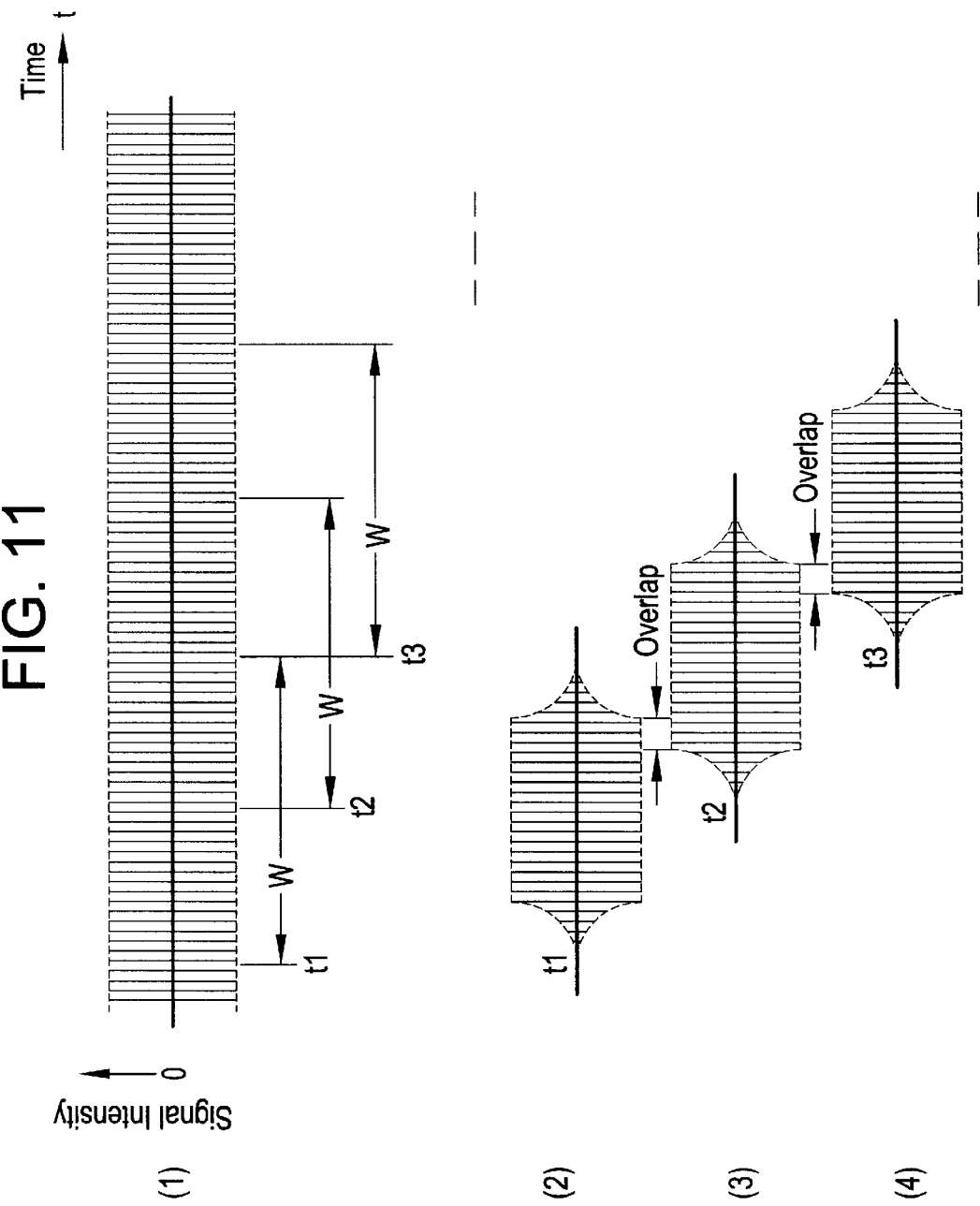
FIG. 11 shows the relationship between Doppler signal cutting and window processing.

FIG. 11 shows the relationship between the cutting of the Doppler signal by the cutting unit 362 and the window processing by the window unit 364. FIG. 11(1) illustrates the cutting of the Doppler signal and FIGS. 11(2), (3) and (4) illustrate the window processing.

As shown, a portion of the Doppler signal of a length corresponding to the window width W is first cut starting at a time t1 position on the time axis. The signal thus cut is window-processed into such a signal as shown in (2). The signal continuously rises from zero in the beginning and continuously decays to zero in the end corresponding to the window profile, and has the same signal intensity as that of the original signal from which the signal is cut, in an intermediate portion between the beginning and end portions. The portion having the same signal intensity as that of the original signal from which the signal is cut will be sometimes referred to as a constant value portion hereinbelow.

Next, a portion of a length corresponding to the window width W is cut starting at a time t2 position on the time axis. The signal thus cut is window-processed into such a signal as shown in (3). This signal also continuously rises from zero in the beginning and continuously decays to zero in the end corresponding to the window profile, and has the constant value portion between the beginning and end portions.

The time t2 is selected such that the cut signal partially overlaps the previously cut signal. The degree of the overlap is such that the constant value portions of the two signals partially overlap after the window processing, as shown in (2) and (3). It should be noted that such partially overlapping cutting is enabled by storing the Doppler signal in the memory.

The cutting unit 362 is an embodiment of the signal cutting means of the present invention. The window unit 364 is an embodiment of the signal cutting means of the present invention.

Next, a portion of a length corresponding to the window width W is cut starting at a time t3 position on the time axis. The signal thus cut is window-processed into such a signal as shown in (4). This signal also continuously rises from zero in the beginning and continuously decays to zero in the end corresponding to the window profile, and has the constant value portion between the beginning and end portions.

The time t3 is selected such that the cut signal partially overlaps the previously cut signal. The degree of the overlap is such that the constant value portions of the two signals partially overlap after the window processing, as shown in (3) and (4). The signal cutting and window processing are sequentially performed thereafter in the same manner.

Such signals are sequentially transformed into frequency-domain signals at the FFT unit 366, conditioned in the frequency domain at the conditioning unit 368, and inversely transformed into a time-domain signal at the iFFT unit 370.

Figure 12:
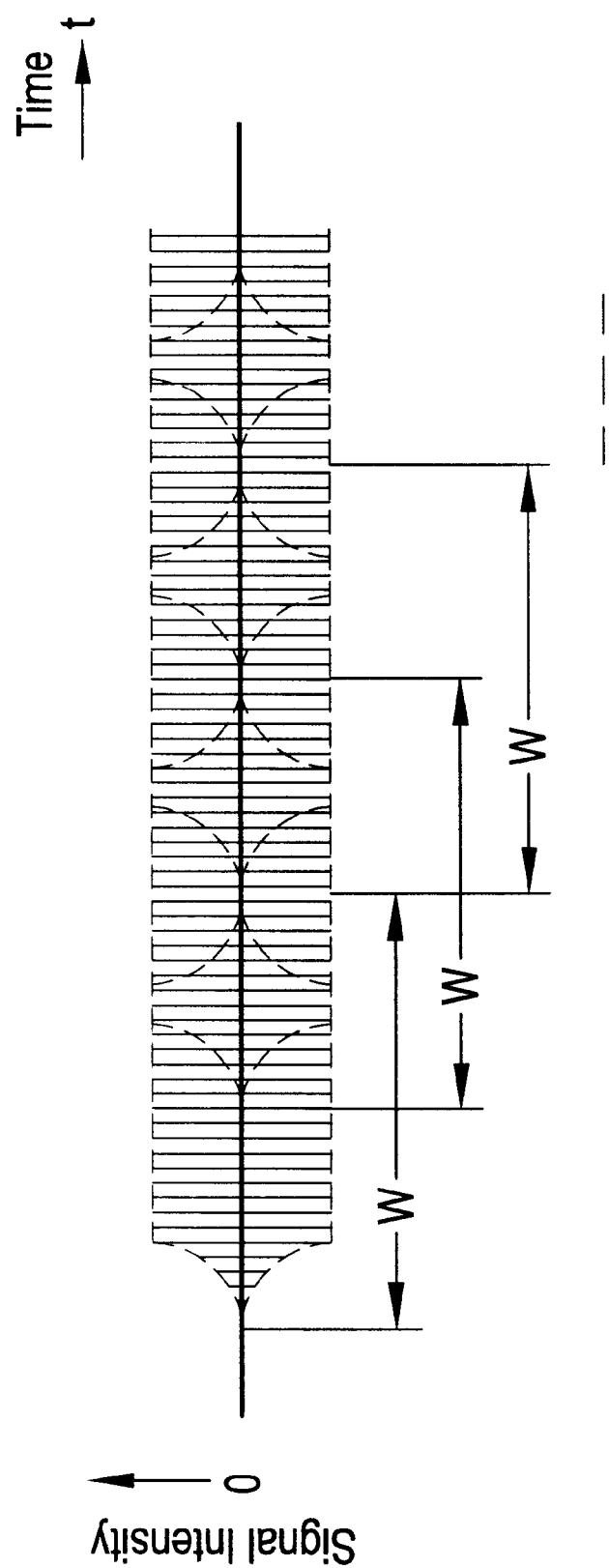
FIG. 12 shows a restored Doppler signal.

Since the consecutive signals input to the FFT unit 366 overlap one another partially at the constant value portion as described above, the consecutive signals that have been inversely transformed by the iFFT unit 370 overlap partially at the constant value portion, as shown in FIG. 12. Thus, a signal including the constant value portion can be obtained. In spite of the window processing, therefore, a Doppler signal unaffected by the window profile can be restored.

Figure 13:
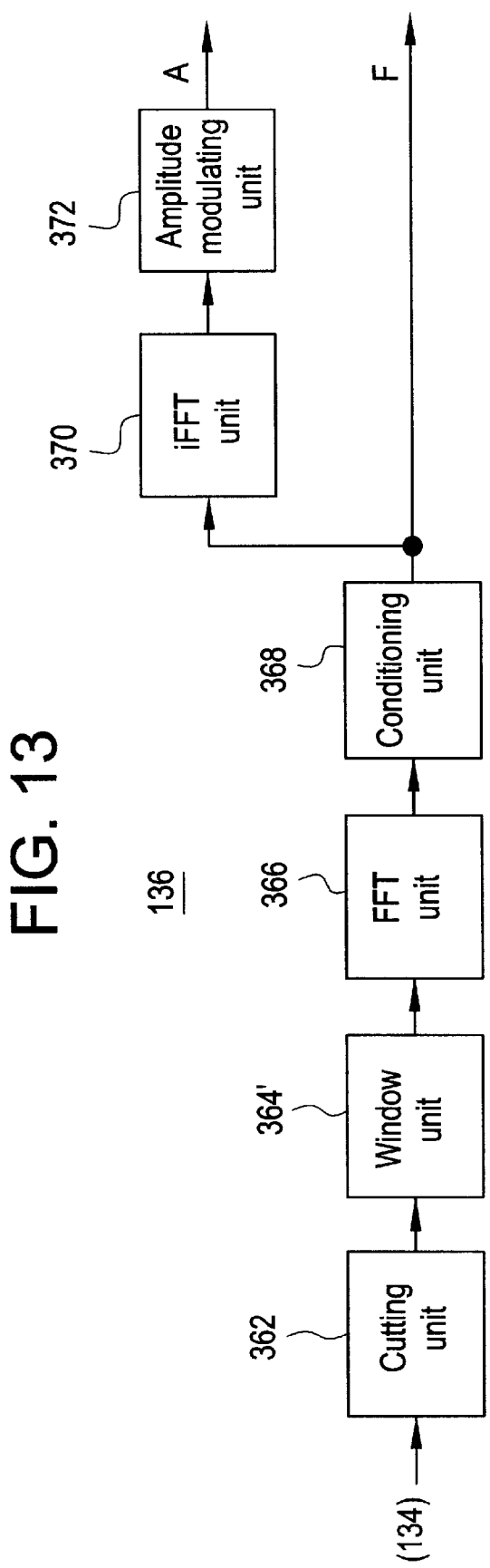
FIG. 13 is a block diagram of another exemplary spectrum processing unit.

FIG. 13 shows a detailed block diagram of another exemplary spectrum processing unit 136, which is an embodiment of the Doppler signal processing apparatus in accordance with the present invention. The configuration of the apparatus represents an embodiment of the apparatus in accordance with the present invention. The operation of the apparatus represents an embodiment of the method in accordance with the present invention.

In FIG. 13, components similar to those shown in FIG. 9 are designated by similar symbols, and explanation thereof will be omitted. As shown, the spectrum processing unit 136 has a window unit 364' employing a window different from that shown in FIG. 9. Moreover, it has an amplitude modulating unit 372 supplied with an output signal from the iFFT unit 370.

Figure 14:
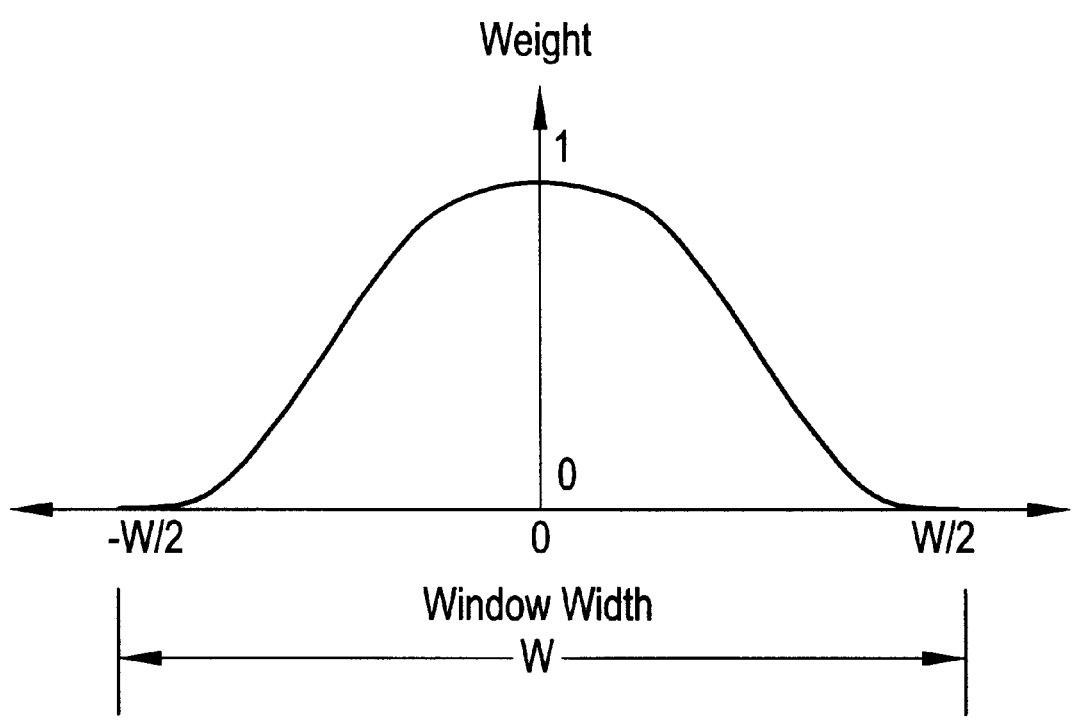
FIG. 14 shows an exemplary window profile.

FIG. 14 shows an exemplary window profile employed by the window unit 364'. As shown, the window is a Hanning window. However, the window is not limited to a Hanning window, and any appropriate window may be employed. While description will be made on an example employing the Hanning window hereinbelow, the same applies to a case in which another window is employed.

FIG. 15 shows the relationship between the cutting of the Doppler signal by the cutting unit 362 and the window processing by the window unit 364'. FIG. 15(1) illustrates the cutting of the Doppler signal and FIGS. 15(2), (3) and (4) illustrate the window processing.

As shown, a portion of the Doppler signal of a length corresponding to the window width W is first cut starting at a time t1 position on the time axis. The signal thus cut is window-processed into such a signal as shown in (2). The signal has an envelope corresponding to the Hanning window.

Next, a portion of a length corresponding to the window width W is cut starting at a time t2 position on the time axis. The signal thus cut is window-processed into such a signal as shown in (3). The signal also has an envelope corresponding to the Hanning window.

The time t2 is selected such that the cut signal partially overlaps the previously cut signal. It should be noted that such partially overlapping cutting is enabled by storing the Doppler signal in the memory.

Next, a portion of a length corresponding to the window width W is cut starting at a time t3 position on the time axis. The signal thus cut is window-processed into such a signal as shown in (4). The signal also has an envelope corresponding to the Hanning window. The time t3 is selected such that the cut signal partially overlaps the previously cut signal. Such signal cutting and window processing are sequentially performed thereafter in the same manner.

Such signals are sequentially transformed into frequency-domain signals at the FFT unit 366, conditioned in the frequency domain at the conditioning unit 368 and inversely transformed into a time-domain signal at the iFFT unit 370.

Since the consecutive signals input to the FFT unit 366 partially overlap one another as described above, the signal that has been inversely transformed by the iFFT unit 370 is amplitude-modulated corresponding to the profile of the Hanning window, as shown in FIG. 16(1). The signal is to be amplitude-modulated by the amplitude modulating unit 372. The amplitude modulation by the amplitude modulating unit 372 is that with an opposite property to cancel the amplitude modulation contained in the output signal from the iFFT unit 370. Such amplitude modulation has a gain profile as shown in FIG. 16(2). This gain profile is constructed by lining up profiles of the inverse function of the Hanning window. It will be easily recognized that when a window other than the Hanning window is employed for the window processing, the inverse function of that window is employed. The amplitude modulating unit 372 is an embodiment of the amplitude modulating means of the present invention.

By such amplitude modulation, the amplitude modulation contained in the output signal from the iFFT unit 370 is canceled out, and a Doppler signal unaffected by the window processing can be restored, as shown in FIG. 16(3).

Accordingly, an acoustic signal based on such a Doppler signal is an accurate acoustic signal without anomaly.

While the present invention has been described with reference to preferred embodiments, various changes or substitutions may be made on these embodiments by those ordinarily skilled in the art pertinent to the present invention without departing from the technical scope of the present invention. Therefore, the technical scope of the present invention encompasses not only those embodiments described above but all that fall within the scope of the appended claims.

Many widely different embodiments of the invention may be constructed without departing from the spirit and the scope of the present invention. It should be understood that the present invention is not limited to the specific embodiments described in the specification, except as defined in the appended claims.

What is claimed is:

1. A Doppler signal processing apparatus for cutting signals of a predetermined length from a time-domain Doppler signal; performing window processing on said cut signals; transforming said window-processed signals into frequency-domain signals by Fourier transformation; inversely transforming said transformed frequency-domain signals into a time-domain signal by inverse Fourier transformation after performing predefined processing on said signals; and outputting said inversely transformed time-domain signal as an acoustic signal, comprising:
    a window processing device for performing said window processing using a window having a profile with a flat top; and
    a signal cutting device for performing said cutting from the Doppler signal such that a former cut signal and a latter cut signal overlap in a portion corresponding to the flat portion of said window.

2. The Doppler signal processing apparatus of claim 1, wherein the profile of said window is generally trapezoidal.

3. The Doppler signal processing apparatus of claim 1, wherein said predefined processing is filtering processing.

4. The Doppler signal processing apparatus of claim 1, wherein said predefined processing is zero-shifting processing.

5. The Doppler signal processing apparatus of claim 1, wherein said predefined processing is correction processing of the output characteristics of said acoustic signal.

6. The Doppler signal processing apparatus of claim 1, wherein the Doppler signal is a Doppler signal of an ultrasonic echo.

7. A Doppler signal processing apparatus for cutting signals of a predetermined length from a time-domain Doppler signal; performing window processing on said cut signals; transforming said window-processed signals into frequency-domain signals by Fourier transformation; inversely transforming said transformed frequency-domain signals into a time-domain signal by inverse Fourier transformation after performing predefined processing on said signals, comprising:
    an output device for outputting said inversely transformed time-domain signal as an acoustic signal; and
    an amplitude modulating device for performing amplitude modulation with a property opposite to that of amplitude modulation by said window processing before outputting said inversely-transformed time-domain signal as the acoustic signal.

8. The Doppler signal processing apparatus of claim 7 wherein the window for performing the window processing on said cut signals is a Hanning window.

9. The Doppler signal processing apparatus of claim 7, wherein said predefined processing is filtering processing.

10. The Doppler signal processing apparatus of claim 7, wherein said predefined processing is zero-shifting processing.

11. The Doppler signal processing apparatus of claim 7, wherein said predefined processing is correction processing of the output characteristics of said acoustic signal.

12. The Doppler signal processing apparatus of claim 7, wherein the Doppler signal is a Doppler signal of an ultrasonic echo.

13. The Doppler signal processing apparatus of claim 7 further comprising a signal cutting device for performing said cutting from the Doppler signal such that a former cut signal and a latter cut signal partially overlap each other.

14. An ultrasonic diagnostic apparatus for transmitting ultrasound and acquiring a Doppler signal of an echo of the ultrasound; cutting signals of a predetermined length from said Doppler signal in a time domain; performing window processing on said cut signals; transforming said window-processed signals into frequency-domain signals by Fourier transformation; inversely transforming said transformed frequency-domain signals into a time-domain signal by inverse Fourier transformation after performing predefined processing on said signals; and outputting said inversely transformed time-domain signal as an acoustic signal, comprising:
    a window processing device for performing said window processing using a window having a profile with a flat top; and
    a signal cutting device for performing said cutting from the Doppler signal such that a former cut signal and a latter cut signal overlap in a portion corresponding to the flat portion of said window.

15. The ultrasonic diagnostic apparatus of claim 14, wherein the profile of said window is generally trapezoidal.

16. The ultrasonic diagnostic apparatus of claim 14, wherein said predefined processing is filtering processing.

17. The ultrasonic diagnostic apparatus of claim 14, wherein said predefined processing is zero-shifting processing.

18. The ultrasonic diagnostic apparatus of claim 14, wherein said predefined processing is correction processing of the output characteristics of said acoustic signal.

19. A method for removing an effect of window processing in imaging systems comprising:
    cutting signals of a predetermined length from a time-domain Doppler signal that is obtained after processing echo signals received from an object;
    performing window processing on said cut signals that are obtained after processing the echo signals received from the object;
    transforming said window-processed signals into frequency-domain signals by Fourier transformation;
    inversely transforming said transformed frequency-domain signals into time-domain signals by inverse Fourier transformation;
    modulating said inversely transformed time-domain signals with a property opposite to that of modulation by said window processing to generate modulated signals; and
    outputting said modulated signals as a Doppler image.

20. A method in accordance with claim 19 wherein said cutting is performed to partially overlap a former cut signal of the Doppler signal with a latter cut signal of the Doppler signal.

* * * * *